US011571108B2

(12) United States Patent
Makino

(10) Patent No.: US 11,571,108 B2
(45) Date of Patent: Feb. 7, 2023

(54) EVALUATION VALUE CALCULATION DEVICE AND ELECTRONIC ENDOSCOPE SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 744 days.

(21) Appl. No.: 16/433,385

(22) Filed: Jun. 6, 2019

(65) Prior Publication Data

US 2019/0282064 A1 Sep. 19, 2019

Related U.S. Application Data

(63) Continuation of application No. 15/505,780, filed as application No. PCT/JP2016/073717 on Aug. 12, 2016, now abandoned.

(30) Foreign Application Priority Data

Aug. 13, 2015 (JP) .................................. 2015-159908

(51) Int. Cl.
*A61B 1/00* (2006.01)
*A61B 1/04* (2006.01)
(Continued)

(52) U.S. Cl.
CPC ...... *A61B 1/00009* (2013.01); *A61B 1/00048* (2013.01); *A61B 1/04* (2013.01);
(Continued)

(58) Field of Classification Search
CPC .......... A61B 1/00009; A61B 1/000095; A61B 5/1032; A61B 5/489; A61B 1/000094; G06T 7/207; G06T 2207/10024
See application file for complete search history.

(56) References Cited

U.S. PATENT DOCUMENTS

| 4,805,016 A | * | 2/1989 | Kato ...................... H04N 9/643 348/E9.04 |
| 4,819,077 A | | 4/1989 | Kikiuchi et al. |

(Continued)

FOREIGN PATENT DOCUMENTS

| CN | 1882278 | 12/2006 |
| CN | 101677753 | 3/2010 |

(Continued)

OTHER PUBLICATIONS

U.S. Appl. No. 15/505,780 to Takao Makino, filed Feb. 22, 2017.
(Continued)

*Primary Examiner* — Timothy J Neal
(74) *Attorney, Agent, or Firm* — Greenblum & Bernstein, P.L.C.

(57) ABSTRACT

An electronic endoscope system includes a plotting unit which plots pixel correspondence points, which correspond to pixels that constitute an intracavitary color image that has a plurality of color components, on a target plane according to color components of the pixel correspondence points, the target plane intersecting the origin of a predetermined color space; an axis setting unit which sets a reference axis in the target plane based on pixel correspondence points plotted on the target plane; and an evaluation value calculating unit which calculates a prescribed evaluation value with respect to the captured image based on a positional relationship between the reference axis and the pixel correspondence points.

9 Claims, 9 Drawing Sheets

(51) Int. Cl.
  *G06T 7/00* (2017.01)
  *G06T 5/00* (2006.01)
  *G06T 7/207* (2017.01)

(52) U.S. Cl.
  CPC ............ *G06T 5/001* (2013.01); *G06T 7/0012* (2013.01); *G06T 7/207* (2017.01); *G06T 2207/10024* (2013.01); *G06T 2207/10068* (2013.01); *G06T 2207/30028* (2013.01); *G06T 2207/30096* (2013.01)

(56) References Cited

U.S. PATENT DOCUMENTS

| | | | |
|---|---|---|---|
| 5,233,416 A | 8/1993 | Inoue | |
| 5,751,261 A | 5/1998 | Zavracky et al. | |
| 6,280,381 B1 | 8/2001 | Malin et al. | |
| 6,602,186 B1 | 8/2003 | Sugimoto et al. | |
| 6,821,245 B2 | 11/2004 | Cline et al. | |
| 6,826,422 B1 | 11/2004 | Motz et al. | |
| 6,937,269 B2 | 8/2005 | Sugimoto et al. | |
| 6,956,602 B2 | 10/2005 | Higuchi et al. | |
| 7,009,639 B1 | 3/2006 | Une et al. | |
| 7,123,288 B2 | 10/2006 | Abe et al. | |
| 7,123,293 B1 | 10/2006 | Uchida | |
| 7,283,858 B2 | 10/2007 | Sendai | |
| 7,289,140 B2 | 10/2007 | Kobayashi | |
| 7,341,557 B2 | 3/2008 | Cline et al. | |
| 7,356,102 B2 | 4/2008 | Morton et al. | |
| 7,713,192 B2 | 5/2010 | Murata | |
| 7,722,534 B2 | 5/2010 | Cline et al. | |
| 7,938,771 B2 | 5/2011 | Homan et al. | |
| 8,225,209 B2 | 7/2012 | Shigemori | |
| 8,253,783 B2 | 8/2012 | Takayama | |
| 8,274,558 B2 | 9/2012 | Takayama | |
| 8,452,092 B2 | 5/2013 | Sasaki | |
| 8,675,058 B2 | 3/2014 | Donomae et al. | |
| 8,743,189 B2 | 6/2014 | Kitamura | |
| 8,775,096 B2 | 7/2014 | Chiba | |
| 8,837,821 B2 | 9/2014 | Hirota et al. | |
| 9,430,833 B2 | 8/2016 | Ikemoto | |
| 9,545,187 B2 | 1/2017 | Chun | |
| 2002/0035330 A1 | 3/2002 | Cline et al. | |
| 2002/0036330 A1 | 3/2002 | Cline et al. | |
| 2002/0105505 A1 | 8/2002 | Sendai | |
| 2002/0177779 A1 | 11/2002 | Adler et al. | |
| 2003/0071895 A1* | 4/2003 | Higuchi .................. H04N 7/183 |
| | | | 348/E7.087 |
| 2004/0073119 A1 | 4/2004 | Mycek et al. | |
| 2004/0073120 A1 | 4/2004 | Modell et al. | |
| 2004/0155957 A1 | 8/2004 | Kobayashi | |
| 2004/0156544 A1* | 8/2004 | Kajihara .................. G06V 10/56 |
| | | | 382/167 |
| 2005/0002586 A1 | 1/2005 | Liege et al. | |
| 2005/0065406 A1 | 3/2005 | Cline et al. | |
| 2006/0087557 A1 | 4/2006 | Donomae et al. | |
| 2006/0178565 A1 | 8/2006 | Matsui et al. | |
| 2006/0193513 A1 | 8/2006 | Minamino | |
| 2006/0211915 A1 | 9/2006 | Takeuchi et al. | |
| 2007/0040906 A1 | 2/2007 | Iketani | |
| 2007/0093691 A1 | 4/2007 | Kobayashi | |
| 2007/0153542 A1 | 7/2007 | Gono et al. | |
| 2007/0161858 A1 | 7/2007 | Homan et al. | |
| 2007/0183162 A1 | 8/2007 | Higuchi | |
| 2008/0228037 A1 | 9/2008 | Cline et al. | |
| 2008/0298037 A1 | 12/2008 | Nakashima | |
| 2009/0109284 A1 | 4/2009 | Takayama | |
| 2009/0237498 A1 | 9/2009 | Modell et al. | |
| 2009/0252406 A1 | 10/2009 | Chiba | |
| 2009/0309961 A1 | 12/2009 | Miyashita | |
| 2010/0007724 A1 | 1/2010 | Takayama | |
| 2010/0074508 A1* | 3/2010 | Shinoda ................ G06V 20/695 |
| | | | 382/133 |
| 2010/0092055 A1 | 4/2010 | Matsuda | |
| 2010/0115469 A1 | 5/2010 | Shigemori | |
| 2010/0158330 A1 | 6/2010 | Guissin et al. | |
| 2010/0177181 A1 | 7/2010 | Ayame et al. | |
| 2010/0179385 A1 | 7/2010 | Murata | |
| 2010/0198010 A1 | 8/2010 | Cline et al. | |
| 2010/0208047 A1 | 8/2010 | Kitamura | |
| 2010/0210904 A1 | 8/2010 | Cline et al. | |
| 2010/0272358 A1 | 10/2010 | Kanda | |
| 2010/0331624 A1 | 12/2010 | Suzuki et al. | |
| 2011/0009886 A1 | 1/2011 | Gagner | |
| 2011/0075901 A1 | 3/2011 | Nakamura | |
| 2011/0176730 A1 | 7/2011 | Sasaki | |
| 2011/0229006 A1 | 9/2011 | Morita | |
| 2011/0242301 A1 | 10/2011 | Morita | |
| 2011/0311133 A1 | 12/2011 | Hirota et al. | |
| 2012/0191365 A1 | 7/2012 | Chiba | |
| 2012/0274754 A1 | 11/2012 | Tsuruoka | |
| 2013/0051642 A1* | 2/2013 | Kanda ...................... G06T 7/90 |
| | | | 382/128 |
| 2014/0320620 A1 | 10/2014 | Ikemoto et al. | |
| 2015/0181185 A1 | 6/2015 | Ikemoto et al. | |
| 2015/0193929 A1 | 7/2015 | Ikemoto | |
| 2016/0007829 A1 | 1/2016 | Chun | |

FOREIGN PATENT DOCUMENTS

| | | |
|---|---|---|
| CN | 101803899 | 8/2010 |
| CN | 102170817 A | 8/2011 |
| CN | 102243762 | 11/2011 |
| EP | 1650980 | 4/2006 |
| EP | 1839558 | 10/2007 |
| EP | 1994878 | 11/2008 |
| EP | 2096859 | 9/2009 |
| EP | 2105086 | 9/2009 |
| EP | 2156784 | 2/2010 |
| EP | 2386999 | 11/2011 |
| EP | 2517614 | 10/2012 |
| JP | S62-266030 | 11/1987 |
| JP | 1-101960 | 4/1989 |
| JP | 2-114931 | 4/1990 |
| JP | 3-4832 | 1/1991 |
| JP | 9-114985 | 5/1997 |
| JP | 2002-172082 | 6/2002 |
| JP | 2002-535023 A | 10/2002 |
| JP | 2004-154176 | 6/2004 |
| JP | 2004-236952 | 8/2004 |
| JP | 2005-504561 A | 2/2005 |
| JP | 2006-061620 A | 3/2006 |
| JP | 2006-142002 | 6/2006 |
| JP | 2006-238321 | 9/2006 |
| JP | 2006-239206 A | 9/2006 |
| JP | 2007-135989 A | 6/2007 |
| JP | 2009-082736 A | 4/2009 |
| JP | 2009-106424 | 5/2009 |
| JP | 2009-297365 | 12/2009 |
| JP | 2010-36017 | 2/2010 |
| JP | 2010-79522 | 4/2010 |
| JP | 2010-115243 | 5/2010 |
| JP | 2010-172673 | 8/2010 |
| JP | 2010-187756 | 9/2010 |
| JP | 2011-143100 | 7/2011 |
| JP | 2011-160848 | 8/2011 |
| JP | 2011-182993 | 9/2011 |
| JP | 2011-218090 | 11/2011 |
| JP | 2011-234931 | 11/2011 |
| JP | 2011-255006 | 12/2011 |
| JP | 2014-18332 | 2/2014 |
| JP | 2014-18333 | 2/2014 |
| WO | 00/42907 | 7/2000 |
| WO | 02/069784 A2 | 9/2002 |
| WO | 2005/045393 A2 | 5/2005 |
| WO | 2005/045393 A3 | 5/2005 |
| WO | 2008/146447 | 12/2008 |
| WO | WO2011/052491 | 5/2011 |

(56) References Cited

FOREIGN PATENT DOCUMENTS

WO          2011/096279        8/2011
WO          WO2014/156938      10/2014

OTHER PUBLICATIONS

U.S. Appl. No. 14/415,378 to Yousuke Ikemoto, filed Jan. 16, 2015.
Search Report issued in WIPO Patent Application No. PCT/JP2016/073717, dated Nov. 1, 2016.
International Search report, with English language translation, in PCT/JP2013/063384, dated Jun. 18, 2013.
International Preliminary Report on Patentability, with Written Opinion and English language translation, in PCT/JP2013/063384, dated Jan. 29, 2015.
Office Action issued in Japan Family member Patent Appl. No. 2012-158248, dated Aug. 18, 2016, along with an English translation thereof.
Search Report issued in European Patent Office (EPO) Patent Application No. 13819790.0, dated Sep. 15, 2016.
Office Action issued in China Family member Patent Appl. No. 201380038083.7, dated Feb. 15, 2017, along with an English translation thereof.
Office Action issued in China Family member Patent Appl. No. 201380037982.5, dated Nov. 30, 2016, along with an English translation thereof.
Office Action issued in China Family member Patent Appl. No. 201380038083.7, dated Sep. 8, 2016, along with an english translation thereof.
Search Report issued by EPO patent office in EPO Patent Application No. 13819629.0, dated Apr. 1, 2016.
Search Report issued by E.P.O. patent office in E.P.O. Patent Application No. 13819790.0, dated Mar. 23, 2016.
Office Action issued in China Family member Patent Appl. No. 201380037982.5, dated Mar. 16, 2016, along with an English translation thereof.

Office Action issued in Japan Family member Patent Appl. No. 2012-158248, dated Feb. 15, 2016, along with an English translation thereof.
Office Action issued in Japan Family member Patent Appl. No. 2012-158249, dated Jun. 1, 2016, along with an English translation thereof.
Chinese Office Action in CN 201380038083.7, dated Feb. 25, 2016, with English language translation.
Office Action in U.S. Appl. No. 14/413,905 dated Dec. 16, 2015.
International Preliminary Report on Patentability in PCT/JP2013/063385, dated Jan. 29, 2015, together with an English translation thereof.
International Search Report in PCT/JP2013/063385, dated Jun. 25, 2013, together with an English translation thereof.
Office Action issued in China Family member Patent Appl. No. 201380038083.7, dated Jul. 3, 2017, along with an english translation thereof.
Golub et al. Molecular classification of cancer: Class discovery and class prediction by gene expression monitoring. Science, vol. 286, 1999, pp. 531-537.
China Office Action, issued in Chinese Application No. 201080048494.0 dated Jan. 28, 2014 along with an English translation thereof.
Etsuhiro Matsuyama et al., "The Standard value of lumber bone mineral density and diagnosis of osteoporosis" Central Japan Journal of Orthopaedic Surgery & Traumatology, Jan. 1, 1994, vol. 37, No. 1, pp. 199 and 200 (With English Translation).
Skoog et al. Fundamentals of Analytical Chemistry, Sixth Edition. New York: Saunders College Publishing, 1992, pp. 8-9.
Search Report issued in WIPO Patent Application No. PCT/JP2016/073718, dated Nov. 1, 2016.
Office Action issued in Chinese family member Patent Appl. No. 201680002618.9, dated Jun. 25, 2018.
Office Action issued in Japanese family member 2016-223699, dated Aug. 7, 2017.
Office Action issued in related Indian family member 3468/DELNP/2012, dated Feb. 14, 2019.
U.S. Appl. No. 15/505,753 to Takao Makino, filed Feb. 22, 2017.

* cited by examiner

EVALUATION VALUE CALCULATION DEVICE AND ELECTRONIC ENDOSCOPE SYSTEM

CROSS REFERENCE TO RELATED APPLICATIONS

This is a continuation application of U.S. patent application Ser. No. 15/505,780, filed Feb. 22, 2017, which is a National Phase application of International Application No. PCT/JP2016/073717, filed on Aug. 12, 2016, and claims the benefit of Japanese Patent Application No. 2015-159908 filed Aug. 13, 2015. The entire disclosure of each of the above-identified applications, including the specification, drawings, and claims, is incorporated herein by reference in its entirety.

TECHNICAL FIELD

The present invention relates to an evaluation value calculation device and an electronic endoscope system for calculating a prescribed evaluation value.

BACKGROUND ART

A lesion site generally has a different color from normal mucosal tissue. In recent years, improvements in the performance of color endoscope apparatuses have made it possible for an operator to identify and diagnose a lesion site whose color is slightly different from normal tissue. However, an operator needs extensive training under the guidance of an expert in order to be able to accurately distinguish a lesion site from normal tissue based on a slight color difference in an image captured by an endoscope and then make a diagnosis. Also, even an experienced operator may not be able to easily identify and diagnose a lesion site based on a slight color difference, and this requires careful work.

In view of this, JP 2014-18332A (referred to hereinafter as "Patent Document 1") is one example of a document that describes a device for scoring a lesion site that appears in a captured image in order to facilitate the diagnosis of a lesion site by an operator. Specifically, with the device described in Patent Document 1, the pixels that constitute an image captured by an endoscope are subjected to tone enhancement processing for applying non-linear gain to the pixel values, the dynamic range is widened in the vicinity of the boundary of a region of pixel values that are to be subjected to lesion site determination, the tone-enhanced pixel data in an RGB space,
which is defined by the three primary colors RGB, is converted to a predetermined color space such as the HIS color space or the HSV color space in order to acquire hue and saturation information, pixels are determined to be or not be lesion site pixels based on the acquired hue and saturation information, and then an evaluation value (lesion index) is calculated based on the number of pixels determined to be lesion site pixels.

SUMMARY OF INVENTION

In evaluation value calculation devices that calculate an evaluation value, typified by the device illustrated in Patent Document 1, even in the case of imaging the same subject, the evaluation value obtained as a result of calculation may change due to differences between electronic endoscope models, change over time, and the like. As a countermeasure, it is conceivable to perform calibration in order to suppress variation in the evaluation value caused by differences between electronic endoscope models, change over time, and the like.

However, in order to perform calibration, it is generally necessary to manufacture a jig dedicated for calibration, and perform a time-consuming operation such as performing calibration imaging using the dedicated jig in advance.

The present invention was achieved in light of the above-described situation, and an object thereof is to provide an evaluation value calculation device and an electronic endoscope system that do not need a dedicated jig or a time-consuming operation when performing calibration.

An electronic endoscope system according to an embodiment of the present invention includes: a plotting means for plotting pixel correspondence points, which correspond to pixels that constitute an intracavitary color image that has a plurality of color components, on a target plane according to color components of the pixel correspondence points, the target plane intersecting an origin of a predetermined color space; an axis setting means for setting a reference axis in the target plane based on pixel correspondence points plotted on the target plane; and an evaluation value calculating means for calculating a prescribed evaluation value with respect to the captured image based on a positional relationship between the reference axis and the pixel correspondence points.

Also, in an embodiment of the present invention, the target plane is a plane that includes an R component axis, for example.

Also, in an embodiment of the present invention, the target plane is a plane that further includes a G component axis, for example.

Also, in an embodiment of the present invention, the reference axis is an axis drawn on a boundary line between a region in which the pixel correspondence points are distributed and a region in which pixel correspondence points are not distributed in the target plane, for example.

Also, in an embodiment of the present invention, a configuration is possible in which the plotting means plots the pixel correspondence points in a predetermined section of the target plane. The section is defined by first and second axes that pass through the origin, for example. Letting the origin be a start point of the first and second axes, and other ends of the first and second axes be end points of the axes, the axis setting means may detect a pixel correspondence point that is located on a line segment connecting the end point of the second axis and the end point of the first axis and that is closest to the end point of the second axis, and set an axis that connects the detected pixel correspondence point and the start point as the reference axis.

Also, in an embodiment of the present invention, a configuration is possible in which the axis setting means partitions the target plane into a first region and a second region using the reference axis. In this case, the evaluation value calculating means calculates the prescribed evaluation value using pixel correspondence points plotted in the first region. Also, the axis setting means sets the reference axis in a manner according to which the number of pixel correspondence points plotted in the second region falls in a predetermined range.

Also, in an embodiment of the present invention, a configuration is possible in which the axis setting means sets the reference axis each time the color image is captured by an image capturing means, or only at a predetermined timing.

Also, in an embodiment of the present invention, a configuration is possible in which the axis setting means calculates a provisional reference axis each time a predetermined timing is reached, and sets the reference axis based on the provisional reference axes calculated at the timings.

Also, in an embodiment of the present invention, the reference axis is an axis having a high correlation with a hue of a mucous membrane in a body cavity, for example.

Also, in an embodiment of the present invention, the prescribed evaluation value is a numerical representation of an abnormal portion in a body cavity, for example.

Also, an evaluation value calculation device according to an embodiment of the present invention includes: a plotting means for plotting pixel correspondence points, which correspond to pixels that constitute an intracavitary color image that has a plurality of color components, on a target plane according to color components of the pixel correspondence points, the target plane intersecting an origin of a predetermined color space; an axis setting means for setting a reference axis in the target plane based on pixel correspondence points plotted on the target plane; and an evaluation value calculating means for calculating a prescribed evaluation value with respect to the captured image based on a positional relationship between the reference axis and the pixel correspondence points.

Also, an evaluation value calculation device according to an embodiment of the present invention includes: an image capturing means for capturing a color image that has R (Red), G (Green), and B (Blue) color components; a plotting means for plotting pixel correspondence points, which correspond to pixels that constitute a captured image obtained by the image capturing means, on a plane according to color components of the pixel correspondence points, the plane including a first axis that is an R component axis and a second axis that is a G component axis and is orthogonal to the first axis; an axis setting means for setting a reference axis that passes through an intersection of the first axis and the second axis in the plane and is not parallel with each of the first axis and the second axis, based on pixel correspondence points plotted on the plane; and an evaluation value calculating means for calculating a prescribed evaluation value with respect to the captured image based on a positional relationship between the reference axis and the pixel correspondence points.

Also, in an embodiment of the present invention, a start point of the first axis and a start point of the second axis are at the same location, for example. In this case, a configuration is possible in which the axis setting means detects a pixel correspondence point that is located on a line segment connecting an end point of the second axis and an end point of the first axis and that is closest to the end point of the second axis, and sets an axis that connects the detected pixel correspondence point and the start point as the reference axis.

Also, in an embodiment of the present invention, a configuration is possible in which the axis setting means sets the reference axis each time the captured image is captured by the image capturing means, or only at a predetermined timing.

Also, in an embodiment of the present invention, a configuration is possible in which the axis setting means calculates a provisional reference axis each time a predetermined timing is reached, and sets the reference axis based on the provisional reference axes calculated at the timings.

Also, in an embodiment of the present invention, the reference axis is an axis having a high correlation with a hue of a mucous membrane in a body cavity, for example.

Also, in an embodiment of the present invention, the prescribed evaluation value is a numerical representation of an abnormal portion in a body cavity, for example.

Also, an evaluation value calculation device according to an embodiment of the present invention may be for incorporation into an electronic endoscope system.

Also, in an embodiment of the present invention, the reference axis is an axis drawn on a boundary line between a region in which the pixel correspondence points are distributed and a region in which pixel correspondence points are not distributed in the target plane.

According to an embodiment of the present invention, an evaluation value calculation device and an electronic endoscope system that do not need a dedicated jig or a time-consuming operation when performing calibration are provided.

DESCRIPTION OF EMBODIMENTS

Hereinafter, embodiments of the present invention will be described with reference to the drawings. Note that an electronic endoscope system is taken as an example of an embodiment of the present invention in the following description.

Configuration of Electronic Endoscope System 1

Figure 1:
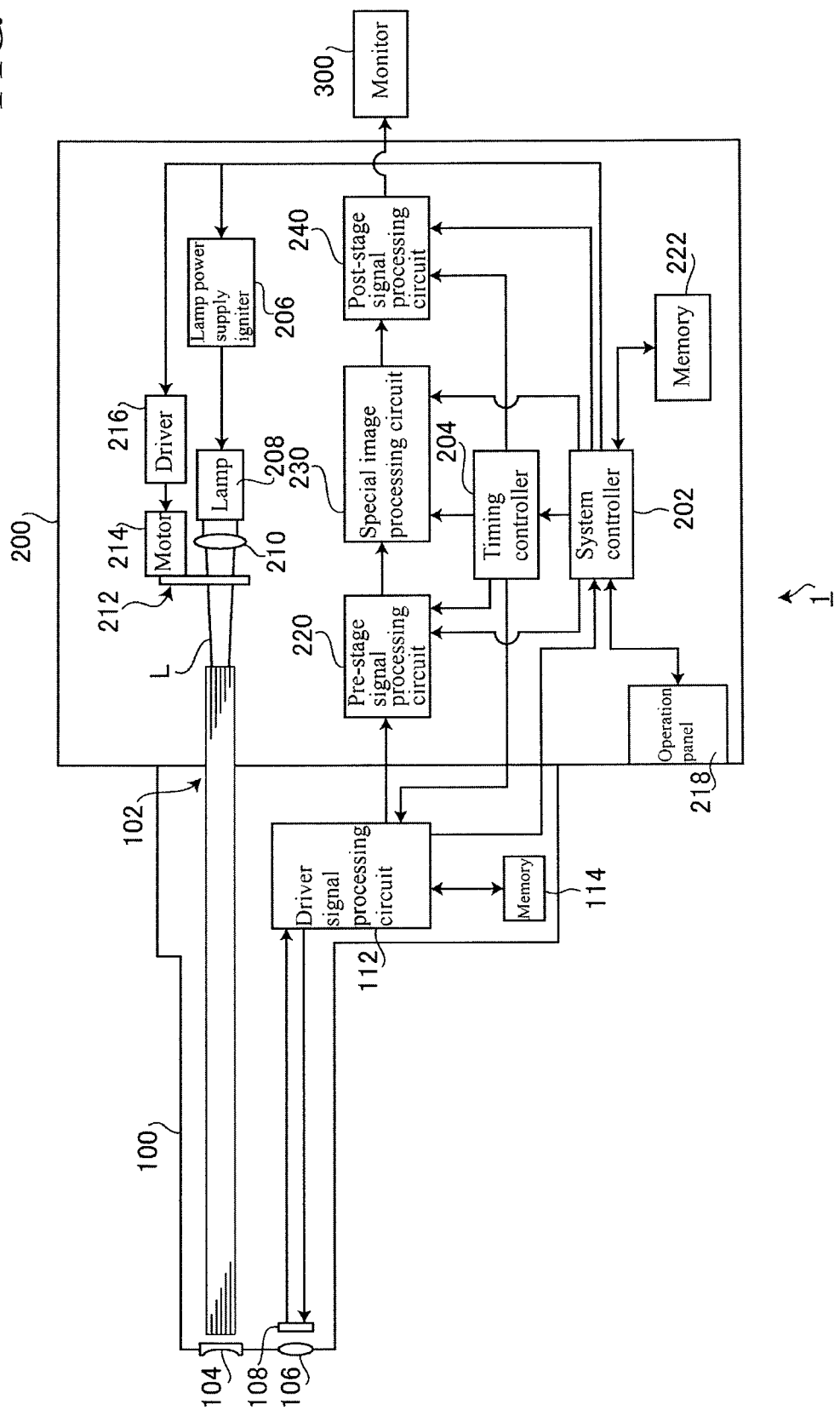
FIG. 1 is a block diagram showing a configuration of an electronic endoscope system according to an embodiment of the present invention.

FIG. 1 is a block diagram showing the configuration of an electronic endoscope system 1 according to an embodiment of the present invention. As shown in FIG. 1, the electronic endoscope system 1 includes an electronic endoscope 100, a processor 200, and a monitor 300.

The processor 200 includes a system controller 202 and a timing controller 204. The system controller 202 executes various programs stored in a memory 222 and performs overall control of the electronic endoscope system 1. Also, the system controller 202 is connected to an operation panel 218. The system controller 202 changes operations of the electronic endoscope system 1 and parameters for various operation in accordance with instructions from an operator that are input using the operation panel 218. One example of an instruction input by an operator is an instruction for switching the operating mode of the electronic endoscope system 1. In the present embodiment, the operating modes include a normal mode and a special mode. The timing controller 204 outputs a clock pulse, which is for adjustment of the timing of the operations of portions, to circuits in the electronic endoscope system 1.

A lamp 208 is activated by a lamp power supply igniter 206, and thereafter emits white light L. The lamp 208 is a high-intensity lamp such as a xenon lamp, a halogen lamp, a mercury lamp, or a metal halide lamp. The white light L emitted by the lamp 208 is condensed by a condensing lens 210 and limited to an appropriate light amount via a diaphragm 212. Note that the lamp 208 may be replaced with a semiconductor light emitting element such as an LD (Laser Diode) or an LED (Light Emitting Diode). Note that a semiconductor light emitting element has features such as having a lower power consumption and smaller heat emission amount than other light sources, and therefore has an advantage of making it possible to acquire bright images while also suppressing power consumption and the heat emission amount. The ability to acquire bright images leads to an improvement in the precision of a later-described inflammation evaluation value.

A motor 214 is mechanically coupled to the diaphragm 212 via transmission mechanisms such as an arm and a gear, which are not shown. The motor 214 is a DC motor for example, and is driven under drive control of a driver 216. The diaphragm 212 is operated by the motor 214, and the opening degree is changed in order to set the images displayed on the display screen of a monitor 300 to an appropriate brightness. The light amount of the white light L emitted by the lamp 208 is limited according to the opening degree of the diaphragm 212. The appropriate image brightness reference is set and changed according to an intensity adjustment operation performed on the operation panel 218 by the operator. Note that the light control circuit for performing intensity adjustment by controlling the driver 216 is a known circuit and will not be described in this specification.

The white light L that passes through the diaphragm 212 is condensed on the entrance end face of an LCB (Light Carrying Bundle) 102 and enters the LCB 102. The white light L that entered the LCB 102 through the entrance end face propagates inside the LCB 102. After propagating inside the LCB 102, the white light L exits through an exit end face of the LCB 102 arranged at the leading end of the electronic endoscope 100, passes through a light distribution lens 104, and illuminates biological tissue. Returning light from the biological tissue illuminated by the white light L passes through an objective lens 106 and forms an optical image on the light receiving surface of a solid-state imaging element 108.

The solid-state imaging element 108 is a single-plate color CCD (Charge Coupled Device) image sensor that has a Bayer pixel arrangement. The solid-state imaging element 108 accumulates charge according to the light quantity of an optical image formed on pixels on the light receiving surface, generates R (Red), G (Green), and B (Blue) image signals, and outputs the image signals. Hereinafter, the image signals of respective pixels (pixel addresses) that are sequentially output by the solid-state imaging element 108 will be referred to as "pixel signals". Note that the solid-state imaging element 108 is not limited to being a CCD image sensor, and may be replaced with a CMOS (Complementary Metal Oxide Semiconductor) image sensor or another type of imaging apparatus. The solid-state imaging element 108 may be an element that includes a complementary color filter. One example of a complementary color filter is a CMYG (Cyan, Magenta, Yellow, Green) filter.

A primary color (RGB) filter has better color characteristics than a complementary color filter. For this reason, the evaluation precision can be improved by performing inflammation evaluation value calculation using RGB image signals obtained by an imaging element that includes a primary color filter. Also, using a primary color filter eliminates the need to perform signal conversion in later-described inflammation evaluation value calculation processing. For this reason, it is possible to suppress the processing burden of inflammation evaluation value calculation.

A driver signal processing circuit 112 is provided in the connection portion of the electronic endoscope 100. Pixel signals from biological tissue illuminated by white light L are input by the solid-state imaging element 108 to the driver signal processing circuit 112 at a frame cycle. The pixel signals input from the solid-state imaging element 108 are output by the driver signal processing circuit 112 to a pre-stage signal processing circuit 220 of the processor 200. Note that the terms "frame" and "field" may be switched in the following description. In the present embodiment, the frame cycle and the field cycle are respectively $\frac{1}{30}$ seconds and $\frac{1}{60}$ seconds.

The driver signal processing circuit 112 also accesses a memory 114 and reads out unique information regarding the electronic endoscope 100. The unique information regarding the electronic endoscope 100 recorded in the memory 114 includes, for example, the pixel count, sensitivity, operable frame rate, and model number of the solid-state imaging element 108. The unique information read out from the memory 114 is output by the driver signal processing circuit 112 to a system controller 202.

The system controller 202 generates control signals by performing various computation based on the unique information regarding the electronic endoscope 100. The system controller 202 uses the generated control signals to control the operations of and the timing of various circuits in the processor 200 so as to perform processing suited to the electronic endoscope that is connected to the processor 200.

A timing controller 204 supplies a clock pulse to the driver signal processing circuit 112 in accordance with timing control performed by the system controller 202. In accordance with the clock pulse supplied from the timing controller 204, the driver signal processing circuit 112 controls the driving of the solid-state imaging element 108 according to a timing synchronized with the frame rate of the images processed by the processor 200.

Operations in Normal Mode

The following describes signal processing operations in the processor 200 in the normal mode.

The pre-stage signal processing circuit 220 performs demosaic processing on R, G, and B pixel signals received from the driver signal processing circuit 112 at the frame cycle. Specifically, R pixel signals are subjected to interpolation processing using G and B surrounding pixels, G pixel signal are subjected to interpolation processing using R and B surrounding pixels, and B pixel signals are subjected to interpolation processing using R and G surrounding pixels. Accordingly, the pixel signals that only had information regarding one color component are converted into pixel data that has information regarding the three R, G, and B color components. Note that in the present embodiment, the pixel data obtained after demosaicing has 8-bit (0-255) information for each of the R, G, and B color components.

The pre-stage signal processing circuit 220 performs predetermined signal processing such as a matrix operation, white balance adjustment processing, and gamma correction processing on the pixel data obtained after demosaic processing, and outputs the resulting data to a special image processing circuit 230.

The special image processing circuit 230 performs pass-through output of the pixel data received from the pre-stage signal processing circuit 220 to the post-stage signal processing circuit 240.

The post-stage signal processing circuit 240 performs predetermined signal processing on the pixel data received from the special image processing circuit 230 to generate screen data for monitor display, and converts the generated monitor display screen data into a predetermined video format signal. The converted video format signal is output to the monitor 300. Accordingly, color images of the biological tissue are displayed on the display screen of the monitor 300.

Operations in Special Mode

Next, signal processing operations in the processor 200 in the special mode will be described.

The pre-stage signal processing circuit 220 performs predetermined signal processing such as demosaic processing, a matrix operation, white balance adjustment processing, and gamma correction processing on pixel signals received from the driver signal processing circuit 112 at the frame cycle, and outputs the resulting data to the special image processing circuit 230.

Special Image Generation Processing

Figure 2:
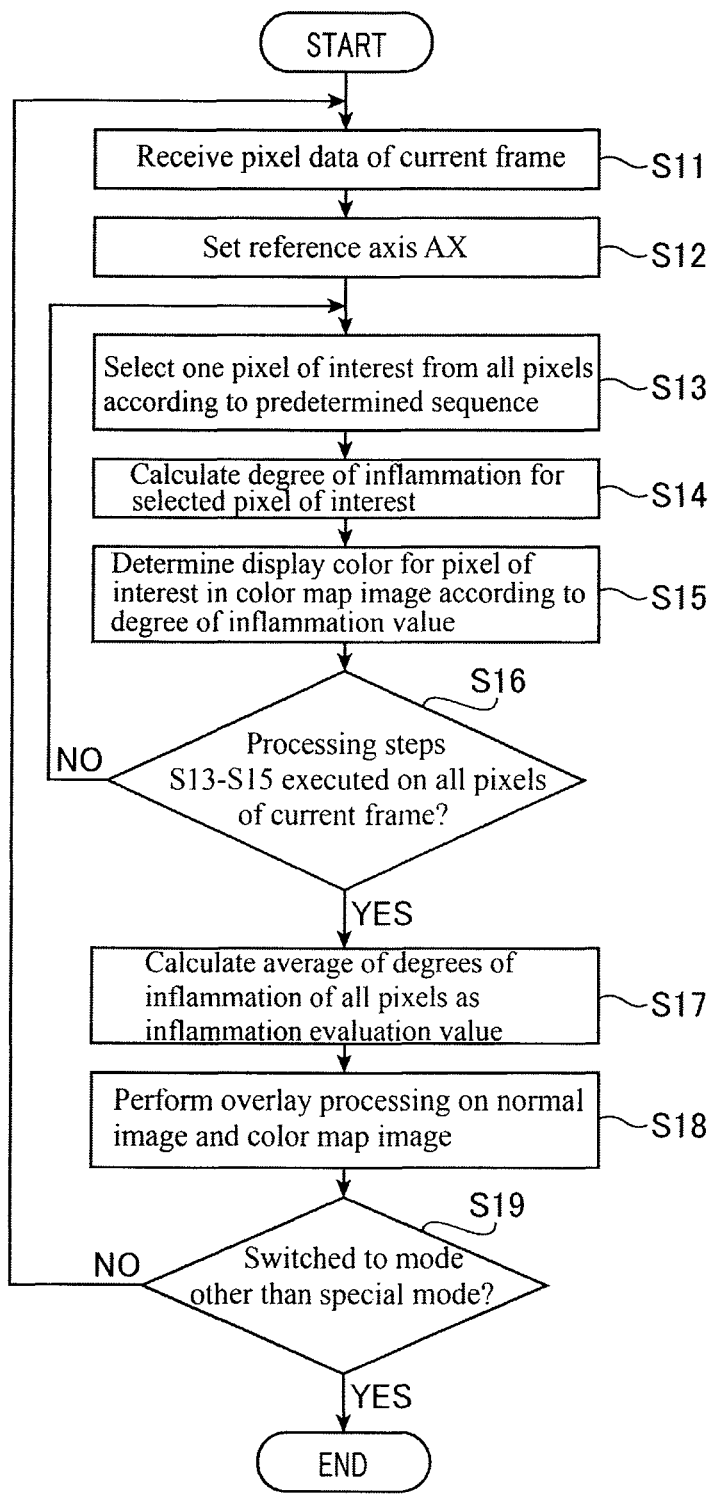
FIG. 2 is a diagram showing a flowchart of special image generation processing performed by a special image processing circuit included in a processor according to an embodiment of the present invention.

FIG. 2 shows a flowchart of special image generation processing performed by the special image processing circuit 230. The special image generation processing in FIG. 2 is started at the time when the operating mode of the electronic endoscope system 1 is set to the special mode, and a freeze button of the electronic endoscope 100 has been pressed (when a still image capture operation has been performed), for example.

S11 in FIG. 2 (Input of Pixel Data of Current Frame)

In this processing step S11, pixel data for each pixel of the current frame (when the capture operation is performed) is received from the pre-stage signal processing circuit 220.

S12 in FIG. 2 (Setting of Reference Axis AX)

Figure 3:
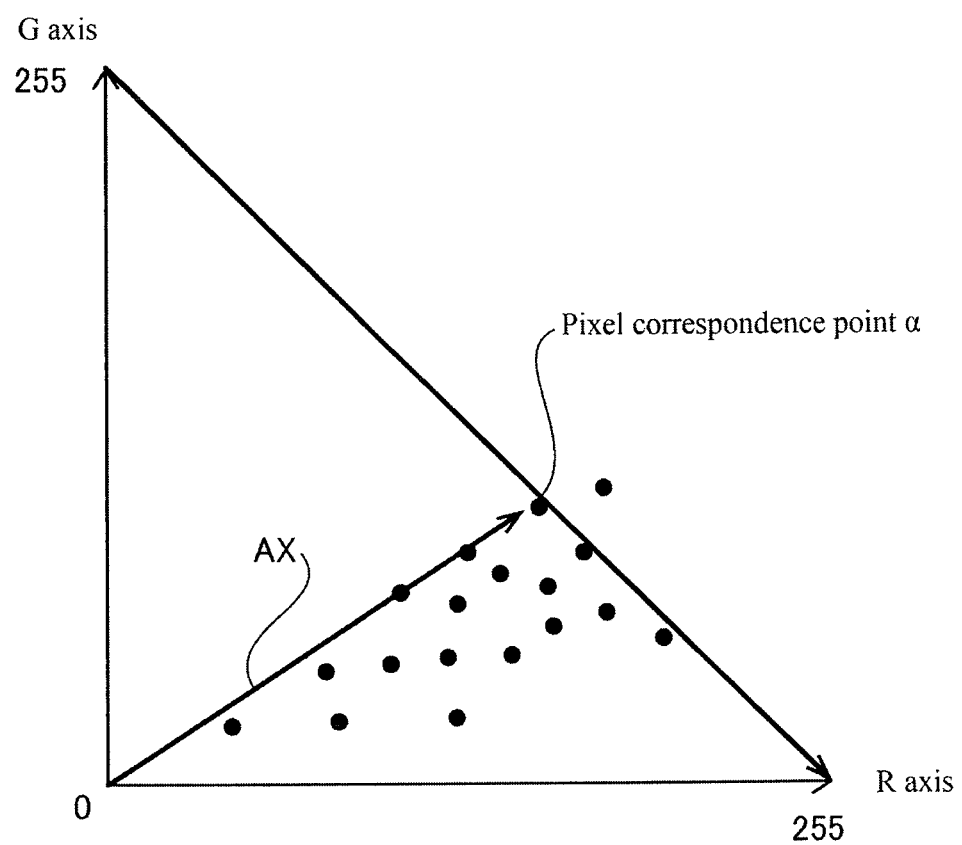
FIG. 3 is a diagram for assisting a description of a reference axis AX setting method in processing step S12 in FIG. 2.

In this processing step S12, the reference axis AX that is to be used when calculating the degree of inflammation of the target illness is set. FIG. 3 is a diagram for assisting the description of a reference axis AX setting method, and shows an RG plane defined by an R axis and a G axis that are orthogonal to each other (more specifically, shows a section in the RG plane defined by the two R and G axes). The R axis is the axis for the R component (R pixel values), and the G axis is the axis for the G component (G pixel values).

In this processing step S12, pixel data (three-dimensional data) for each pixel in the RGB space defined by the three primary colors RGB is converted into RG two-dimensional data and plotted in the RG plane according to the R and G pixel values as shown in FIG. 3. Hereinafter, for the sake of convenience in the description, the points corresponding to pixel data plotted on the RG plane will be referred to as "pixel correspondence points". Note that the operation of plotting the pixel data on the RG plane, which is executed in this processing step S12, is performed by a plotting means. Also, the operation of setting the reference axis AX on the RG plane is performed by an axis setting means.

In this way, in this processing step S12, pixel of interest data (three-dimensional data) in the RGB space is orthographically projected onto the RG plane, and the pixel of interest correspondence points (two-dimensional data) are the feet of vertical lines dropped onto the RG plane from the points in the RGB plane that correspond to the pixel of interest data.

Due to influences such as hemoglobin coloring, the R component is dominant over the other components (G component and B component) in the body cavity of the patient that is to be imaged, and the redness (i.e., R component) typically increases the more intense the inflammation is. For this reason, the R axis value of the pixel correspondence point is basically thought to be proportional to the degree of inflammation. However, in images captured inside a body cavity, the hue varies according to imaging conditions that influence brightness (e.g., degree of illumination with white light L). For example, shaded portions not reached by the white light L are black (achromatic), and portions where the white light L strikes intensely and is specularly reflected are white (achromatic). In other words, depending on the degree of illumination with the white light L, the R axis value of the pixel correspondence point may take a value that has no correlation with the degree of inflammation. Accordingly, it is difficult to precisely evaluate the degree of inflammation with only the R component.

Generally, normal sites inside a body cavity that are not inflamed are sufficiently covered by a mucous membrane. In contrast, abnormal sites inside a body cavity that are inflamed are not sufficiently covered by a mucous membrane. The mucous membrane is thinner the greater the degree of inflammation is at an abnormal site such as a lesion site. A mucous membrane is basically white in color, but has a slightly yellowish hue, and the hue (yellow hue) that appears in an image varies according to the darkness/lightness (membrane thickness). Accordingly, the darkness/lightness of the mucous membrane is also thought to be an indicator for evaluating the degree of inflammation.

In view of this, in this processing step S12, a reference axis AX is set as shown in FIG. 3 so as to pass through the intersection (origin) of the R axis and the G axis in the RG plane and also not be parallel with each of the R axis and the G axis. Specifically, the pixel correspondence point that is located on a line segment connecting the end point of the G axis and the end point of the R axis, both of which have the same start point (both start points being the origin (0,0)), and that is the closest to the end point of the G axis (in the example in FIG. 3, the pixel correspondence point indicated with the reference sign a) is detected. Next, the axis that connects the detected pixel correspondence point a and the start points of the R axis and the G axis (i.e., the origin (0,0)) is set as the reference axis AX.

The reference axis AX is the variation axis of the hue in which the color component that is a mixture of the R component and the G component (i.e., the yellow component) is dominant, and has a high correlation with mucous membrane darkness/lightness (mucous membrane hue). As a result of the inventor of the present invention analyzing many sample images taken inside body cavities, it was found that, as shown in the example in FIG. 3, in the RG plane, when an axis is drawn between the start points of the R axis and the G axis and the pixel correspondence point a that is located on a line segment connecting the end point of the G axis and the end point of the R axis and is located the closest to the end point of the G axis, two regions separated by the drawn axis (reference axis AX) appear, namely a region in which pixel correspondence points are distributed and a region in which pixel correspondence points are not distributed. The reference axis AX that has a high correlation with change in the mucous membrane hue will be referred to hereinafter as the "mucous membrane variation axis" for the sake of convenience in the description.

For better understanding, it is thought that the pixel correspondence points in the RG plane are distributed in the region sandwiched between the axes indicating blood and a mucous membrane. For this reason, the boundary line between the region in which pixel correspondence points are distributed and the region in which pixel correspondence points are not distributed corresponds to the axis that indicates the mucous membrane (mucous membrane variation axis). Given that the point indicated by the reference sign a is a point located on the boundary line, the reference axis AX that connects the point a and the origin is defined as the mucous membrane variation axis.

Additionally, the region in which pixel correspondence points are distributed is the region in the RG plane that indicates hues that can appear when imaging a target illness. Also, the region in which pixel correspondence points are not distributed is the region in which the RG plane that indicates hues that cannot appear when imaging a target illness.

In this way, in the present embodiment, in the process of executing the special image generation processing shown in FIG. 2, calibration (setting of the reference axis AX that can change due to differences between models, change over time, and the like in the electronic endoscope 100) is automatically executed using an actual intracavitary captured image. Accordingly, there is no need for a troublesome operation and a dedicated tool that are conventionally necessary for calibration.

S13 in FIG. 2 (Selection of Pixel of Interest)

In this processing step S13, one pixel of interest is selected from among all of the pixels in accordance with a predetermined sequence. Hereinafter, for the sake of convenience in the description, the points corresponding to pixel of interest data plotted on the RG plane (and on the later-described R-mucous membrane plane) will be referred to as "pixel of interest correspondence points".

S14 in FIG. 2 (Calculation of Degree of Inflammation)

Figure 4:
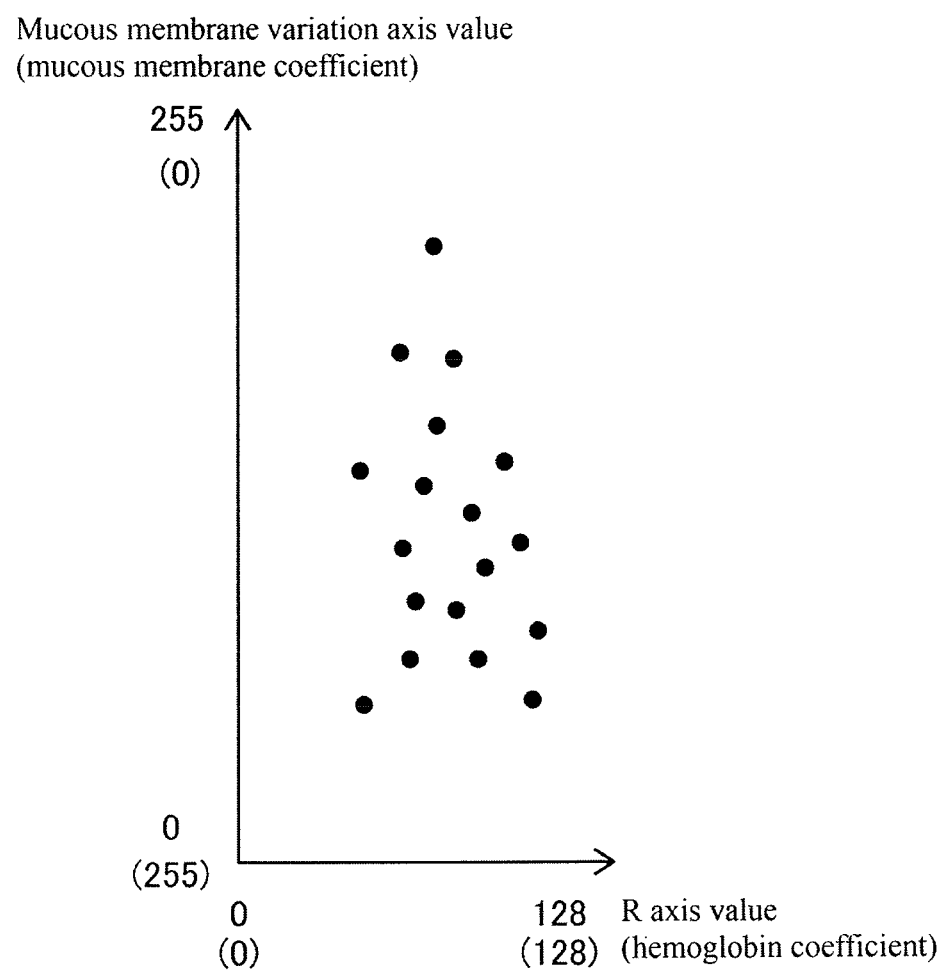
FIG. 4 is a diagram for assisting a description of degree of inflammation calculation processing in processing step S14 in FIG. 2.
Figure 5:
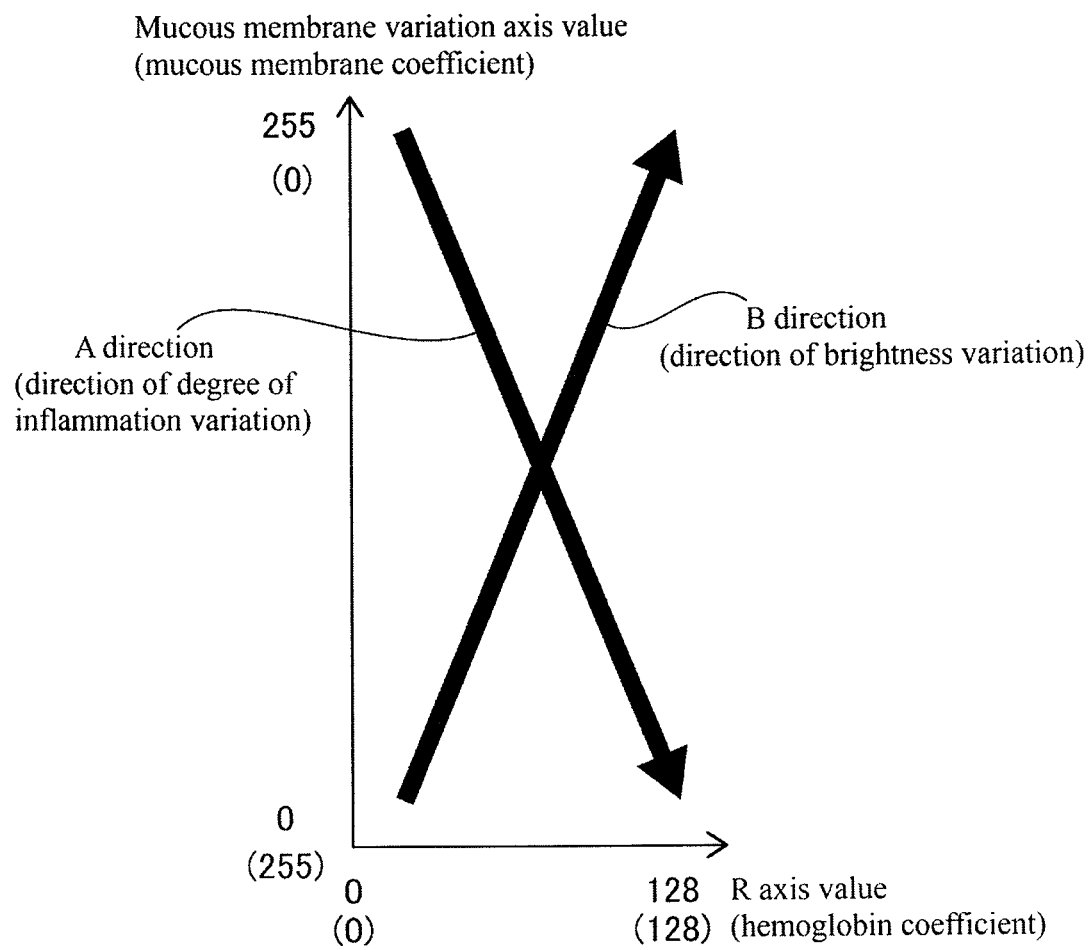
FIG. 5 is a diagram for assisting a description of degree of inflammation calculation processing in processing step S14 in FIG. 2.

In this processing step S14, the degree of inflammation is calculated for the pixel of interest that was selected in processing step S13 (selection of pixel of interest). FIGS. 4 and 5 are diagrams for assisting the description of degree of inflammation calculation processing.

In this processing step S14, as shown in FIG. 4, the plane in which the R axis and the mucous membrane variation axis are orthogonal (referred to hereinafter as the "R-mucous membrane plane" for the sake of convenience in the description) is defined, and the pixel of interest data (pixel of interest correspondence points) plotted on the RG plane are subjected to projective transformation (orthographic projective transformation) onto the R-mucous membrane plane. Note that as a result of the inventor of the present invention analyzing many sample images of mucous membranes inside body cavities, it was found that the R axis values of the pixel correspondence points that were subjected to projective transformation onto the R-mucous membrane plane are under 128 at their highest. In view of this, in the R-mucous membrane plane, the R axis is compressed to 7 bits in order to reduce the calculation processing burden. Also, the mucous membrane variation axis is expressed in 8 bits.

Next, two coefficients (hemoglobin coefficient and mucous membrane coefficient) that increase in value as the degree of inflammation rises are applied to the pixel of interest correspondence points, and the applied hemoglobin coefficient and mucous membrane coefficient are multiplied.

The hemoglobin coefficient is a coefficient that rises in proportion to the R axis value, and is correlated with the degree of inflammation. In the present embodiment, the hemoglobin coefficient matches the R axis value. For example, if the R axis value of the pixel of interest correspondence point is 10, "10" is applied as the hemoglobin coefficient to the pixel of interest correspondence point, and if the R axis value of the pixel of interest correspondence point is 250, "250" is applied as the hemoglobin coefficient to the pixel of interest correspondence point.

The mucous membrane coefficient is a coefficient that decreases as the mucous membrane variation axis value rises, and in the present embodiment, it is a value obtained by subtracting the mucous membrane variation axis value from the value of 255. From another viewpoint, the mucous membrane coefficient is a coefficient that increases as the mucous membrane variation axis value decreases, and rises the thinner the mucous membrane is (the greater the degree of inflammation is). For example, if the mucous membrane variation axis value of the pixel of interest correspondence point is 10, "245(=255−10)" is applied as the mucous membrane coefficient to the pixel of interest correspondence point, and if the mucous membrane variation axis value of the pixel of interest correspondence point is 250, "5(=255−250)" is applied as the mucous membrane coefficient to the pixel of interest correspondence point.

The multiplied value of the hemoglobin coefficient and the mucous membrane coefficient is divided by 128, which is the maximum value of the hemoglobin coefficient. Accordingly, a degree of inflammation that falls within the range of 0 to 255 is calculated for the pixel of interest.

In this way, in this processing step S14, only division that can be performed by bit shift calculation is performed when calculating the degree of inflammation. For this reason, floating-point calculation is not necessary, and the processing burden in degree of inflammation calculation is low.

FIG. 5 is a diagram illustrating the relationship between the degree of inflammation calculated in this processing step S14 and brightness in a intracavitary captured image.

In FIG. 5, the degree of inflammation increases the farther the pixel corresponding to the pixel correspondence point is located in the direction indicated by an arrow A. In other words, in FIG. 5, the degree of inflammation decreases the farther away the pixel corresponding to the pixel correspondence point is located in the upper left region where the hemoglobin coefficient and the mucous membrane coefficient are both low, and increases the farther away the pixel corresponding to the pixel correspondence point is located in the lower right region where the hemoglobin coefficient and the mucous membrane coefficient are both high.

On the other hand, if brightness in the intracavitary captured image changes according to the degree of illumination with white light L, the hue in the captured image is influenced by individual differences, the imaging location, the state of inflammation, and the like, but is basically thought to change in the same manner for each of the color components. According to this thinking, the intracavitary captured image increases in brightness the farther away the pixel corresponding to the pixel correspondence point is located in the direction indicated by an arrow B in FIG. 5. In other words, in FIG. 5, the intracavitary captured image decreases in brightness the farther away the pixel corresponding to the pixel correspondence point is located in the lower left region where the R axis and mucous membrane variation axis values are both low, and increases in brightness the farther away the pixel corresponding to the pixel correspondence point is located in the upper right region where the R axis and mucous membrane variation axis values are both low.

As shown in FIG. 5, in the R-mucous membrane plane, the direction of high correlation with change in the degree of inflammation (arrow A direction) is approximately orthogonal to the direction of high correlation with change in brightness in a captured image (arrow B direction). Based on this, it is understood that the degree of inflammation calculated in this processing step S14 is a value that is substantially not influenced by change in brightness in the captured image.

S15 in FIG. 2 (Determination of Display Color in Color Map Image)

In the present embodiment, it is possible to display a color map image obtained by mosaicking a captured image in display colors that correspond to the degree of inflammation. In order to enable the display of a color map image, a table of correspondence between degree of inflammation values and predetermined display colors is stored in a storage region such as the memory 222. In this table, a display color is associated with each group of 5 values, for example. For example, yellow is associated with the range of degree of inflammation values 0 to 5, different display colors are associated with groups of five higher values according to the color order in the hue circle, and red is associated with the range of values 250 to 255.

In this processing step S15, the display color in the color map image for the pixel of interest selected in processing step S13 (selection of pixel of interest) is determined to be, based on the above-described table, the color that corresponds to the value of the degree of inflammation of the pixel of interest that was calculated in processing step S14 (calculation of degree of inflammation).

S16 in FIG. 2 (Determination of Completion of Execution of Processing for all Pixels)

In this processing step S16, it is determined whether or not processing steps S13 to S15 have been executed for all of the pixels in the current frame.

If a pixel not yet subjected to processing steps S13 to S15 remains (S16: NO), the procedure in the special image generation processing in FIG. 2 returns to processing step S13 (selection of pixel of interest) in order to execute processing steps S13 to S15 on the next pixel of interest.

S17 in FIG. 2 (Calculation of Inflammation Evaluation Value)

Step S17 of this processing is executed if it is determined in processing step S16 (determination of completion of execution of processing for all pixels) that processing steps S13 to S15 have been executed on all of the pixels in the current frame (S16: YES). In this processing step S17, an average value obtained by averaging the degree of inflammation of all of the pixels in the current frame is calculated as the overall inflammation evaluation value of the captured image, and display data for the calculated inflammation evaluation value (example of display data: Score: OO) is generated. Note that the operation of calculating an inflammation evaluation value as a prescribed evaluation value for a color image, which is executed in this processing step S17, is performed by an evaluation value calculating means.

S18 in FIG. 2 (Overlay Processing)

In this processing step S18, a coefficient is set as the ratio for overlaying a normal image, which is based on pixel data received from the pre-stage signal processing circuit 220 (i.e., pixel data having the three R, G, and B color components), and a color map image, which is based on pixel data including predetermined display colors that were determined in processing step S15 (determination of display color in color map image), and the former pixel data (normal pixel data) and the latter pixel data (color map pixel data) are added based on the coefficient. The setting of the coefficient can be appropriately changed by a user operation. In the case of a desire to display the normal image more, the coefficient for the normal pixel data is set higher, and in the case of a desire to display the color map image more, the coefficient for the color map pixel data is set higher.

S19 in FIG. 2 (End Determination)

In this processing step S19, it is determined whether or not the operating mode of the electronic endoscope system 1 has been switched to a mode other than the special mode. If it is determined that the operating mode has not been switched to another mode (S19: NO), the procedure in the special image generation processing in FIG. 2 returns to processing step S11 (input of pixel data of current frame). However, if it is determined that the operating mode has been switched to another mode (S19: YES), the special image generation processing in FIG. 2 ends.

Screen Display Example

The post-stage signal processing circuit 240 generates display data for an overlay image including the normal image and the color map image based on the pixel data obtained by the addition processing in processing step S18 (overlay processing) in FIG. 2, performs masking processing for masking the peripheral region of the display screen of the monitor 300 (periphery of the image display region), and furthermore generates monitor display screen data in which the inflammation evaluation value is superimposed on the mask region generated by the masking processing. The post-stage signal processing circuit 240 converts the generated monitor display screen data into a predetermined video format signal, and outputs the signal to the monitor 300.

Figure 6:
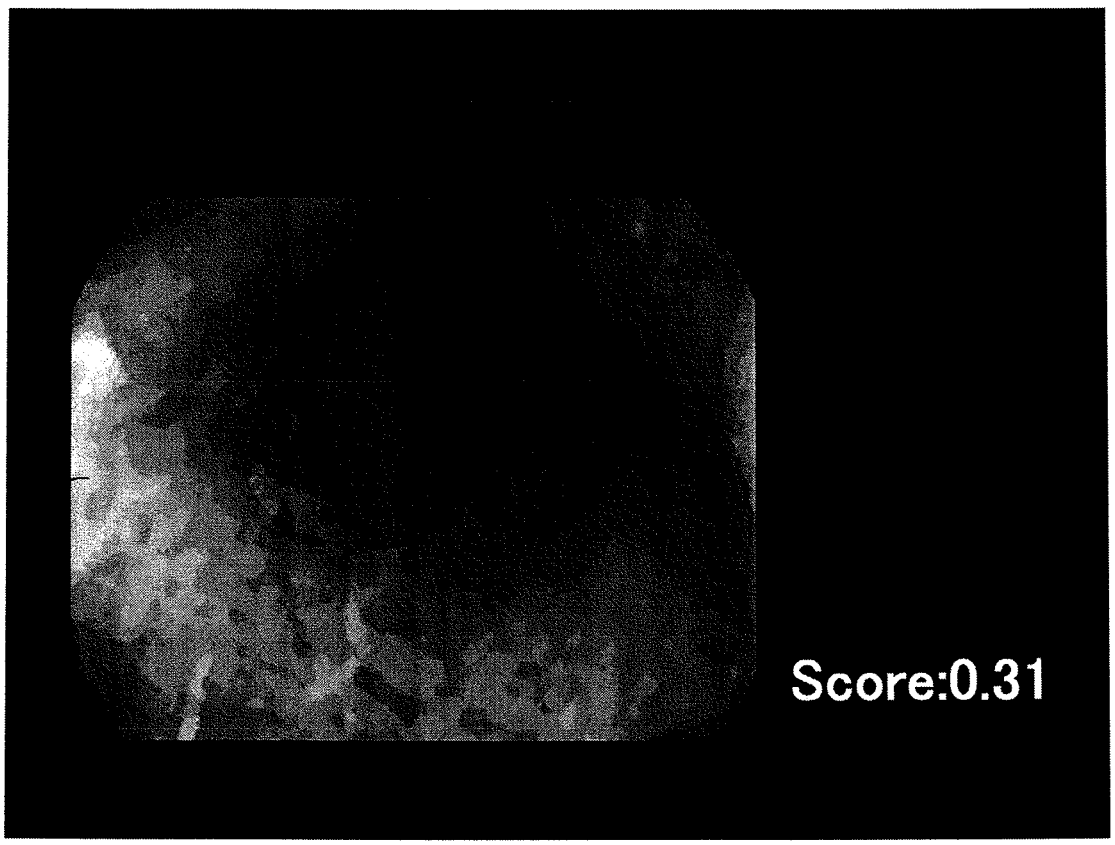
FIG. 6 is a diagram showing an example of a display screen displayed on a monitor display screen in a special mode according to an embodiment of the present invention.

FIG. 6 shows an example of screen display in the special mode. As shown in FIG. 6, the display screen of the monitor 300 includes the intracavitary captured image (overlay image in which the normal image and the color map image are overlaid) in the central region, and a masked screen region surrounding the image display region. The inflammation evaluation value (score) is also displayed in the mask region.

In this way, according to the present embodiment, there is no need to perform complex color space transformation processing, nonlinear calculation processing such as tone enhancement processing, or the like, and an inflammation evaluation value (here, a value correlated with increase/decrease in the hemoglobin coloring of an imaging site) is obtained by merely performing simple calculation processing. In other words, the amount of hardware resources needed for calculation of an inflammation evaluation value is significantly suppressed. Also, the inflammation evaluation value substantially does not vary according to imaging conditions that influence the brightness of the intracavitary captured image (e.g., the degree of illumination with irradiation light), and therefore the operator can make a more objective and accurate diagnosis regarding inflammation.

Also, in the present embodiment, calibration is automatically executed in the processor 200 in the process of calculating a degree of inflammation, thus eliminating the need for a dedicated jig or a time-consuming operation that have conventionally been required for calibration.

Also, the electronic endoscope system according to the present embodiment achieves effects and problem solutions such as the following in the applicable technical fields.

First, the electronic endoscope system according to the present embodiment is a diagnostic aid for early discovery of an inflammatory illness.

Second, according to the configuration of the present embodiment, it is possible to display a screen showing the degree of inflammation or enhance the image in a region in which inflammation is occurring, such that the operator can discover mild inflammation that is difficult to view. In particular, mild inflammation is difficult to distinguish from a normal site, and therefore the effects achieved by the configuration of the present embodiment regarding the evaluation of mild inflammation are remarkable.

Third, according to the configuration of the present embodiment, it is possible to provide the operator with an objective evaluation value as an evaluation of the degree of inflammation, thus making it possible to reduce differences in diagnoses among operators. In particular, there is a large advantage of being able to provide an operator having little experience with an objective evaluation value obtained by the configuration of the present embodiment.

Fourth, according to the configuration of the present embodiment, the burden of image processing is reduced, thus making it possible to perform real-time display of images of an inflamed site. This makes it possible to improve diagnosis precision.

Fifth, according to the configuration of the present embodiment, the processing burden of evaluation value calculation is reduced in comparison with the background technology described above, thus making it possible to display a color map image (image showing the degree of inflammation) and a normal image side-by-side or in a composited manner without lag. For this reason, it is possible to display a color map image without extending the inspection time, thus making it possible to avoid an increase in the burden on the patient.

The site that is to be observed in the present embodiment is a respiratory organ or the like, or a digestive organ or the like, for example. Here, "respiratory organ or the like" includes the lungs, the ears, the nose, and the throat, for example. "Digestive organ or the like" includes the large intestine, the small intestine, the stomach, the duodenum, and the uterus, for example. The electronic endoscope system according to the present embodiment is thought to have even more remarkable effects when the observation target is the large intestine. The following are specific reasons for this.

The large intestine is susceptible to diseases that can be evaluated using inflammation as a reference, and the advantage of discovering inflamed sites is greater than in the case of other organs. In particular, the inflammation evaluation value obtained by the present embodiment is effective as an indicator of inflammatory bowel disease (IBD), which is typified by ulcerative colitis. A method of treatment has not been established for ulcerative colitis, and therefore using the electronic endoscope system having the configuration of the present embodiment is very effective in making an early diagnosis and suppressing the progression of the illness.

The large intestine is a narrower and longer organ than the stomach and the like, and the obtained images have greater depth and are darker as the depth increases. According to the configuration of the present embodiment, it is possible to suppress variation in the evaluation value caused by changes in the brightness in the image. Accordingly, when the electronic endoscope system according to the present embodiment is applied to the observation of the large intestine, the effects of the present embodiment are remarkable. In other words, the electronic endoscope system according to the present embodiment is preferably a respiratory organ electronic endoscope system or a digestive organ electronic endoscope system, and is more preferably a large intestine electronic endoscope system.

Also, although mild inflammation is generally difficult to diagnose, according to the configuration of the present embodiment, by displaying the results of degree of inflammation evaluation on the screen for example, it is possible to avoid a situation in which the operator misses mild inflammation. In particular, in the case of mild inflammation, the determination criteria are not clear, and this is a factor that causes a large amount of individual differences between operators. In this regard as well, according to the configuration of the present embodiment, it is possible to provide the operator with an objective evaluation value, thus making it possible to reduce variation in diagnoses caused by individual differences.

Note that the above-described configuration of the present embodiment is applicable to the calculation of an evaluation value of not only the degree of inflammation, but also cancer, polyps, and various other lesions that are accompanied by a color change, and advantageous effects similar to those described above can be achieved in these other cases as well. In other words, the evaluation value of the present embodiment is preferably an evaluation value for a lesion that is accompanied by a color change, and includes an evaluation value of at least any of inflammation, cancer, and polyps.

An illustrative embodiment of the present invention has been described above. The embodiments of the present invention are not limited to the embodiment described above, and various changes can be made without departing from the scope of the technical idea of the present invention. For example, appropriate combinations of embodiments and the like explicitly given as examples in this specification and obvious embodiments and the like are also encompassed in embodiments of the present invention.

In the above embodiment, calibration (setting of the reference axis AX) is executed only at the timing when the freeze button of the electronic endoscope 100 is pressed (i.e., when a still image is captured), but the present invention is not limited to this. Calibration may be executed one time during moving image shooting (e.g., when a predetermined time has elapsed since power on) or constantly (each time a frame image is captured).

In the above embodiment, calibration (setting of the reference axis AX) is executed based on information included in a captured image corresponding to one frame, but the present invention is not limited to this. For example, biological tissue in a body cavity is covered by a mucous membrane and has glossiness. For this reason, when irradiation light is specularly reflected and then incident on the light receiving surface of the imaging element, there are cases where blown-out highlights appear at biological tissue located in a specular reflection region, and a proper observation image is not obtained. In view of this, in another embodiment, a provisional reference axis AX is calculated each time a frame image is captured when the freeze button of the electronic endoscope 100 is pressed, for example. Next, when a provisional reference axis AX has been calculated for captured images corresponding to n (n being a natural number of 2 or more) frames, the reference axis AX (definitive value) is set based on the n provisional reference axes AX that were calculated. The reference axis AX (definitive value) is, for example, the median value or the average value of the n provisional reference axes AX.

In the above embodiment, the inflammation evaluation value is calculated using the R component and the G component (RG two-dimensional color space) included in the pixels, but in another embodiment, by using another two-dimension color space such as RB in place of the RG two-dimensional color space, or a three-dimensional color space such as HSI, HSV, or Lab, it is possible to calculate an evaluation value that corresponds to the other color space and is related to a target illness different from that of the above embodiment.

Although an evaluation value for inflammation or the like is calculated using R, G, and B primary color components in the above embodiment, the configuration for calculating an evaluation value of the present invention is not limited to using the R, G, and B primary color components. A configuration is possible in which in place of using the R, G, and B primary color components, the C, M, Y, and G (Cyan, Magenta, Yellow, and Green) complementary color components are used to calculate an evaluation value for inflammation or the like with a method similar to that of the above embodiment.

Although the light source portion that includes the lamp power supply igniter 206, the lamp 208, the condensing lens 210, the diaphragm 212, the motor 214, and the like is provided integrated with the processor in the above embodiment, the light source portion may be provided as a device that is separate from the processor.

As described in the above embodiment, a CMOS image sensor may be used in place of a CCD image sensor as the solid-state imaging element 108. In general, with a CMOS image sensor, the image tends to be overall darker than in the case of a CCD image sensor. Accordingly, with the configuration of the above embodiment, the advantageous effect of being able to suppress variation in the evaluation value caused by image brightness is even more remarkable in a situation where a CMOS image sensor is used as the solid-state imaging element.

In order to precisely make a diagnosis, it is preferable to obtain high-definition images. Accordingly, from the viewpoint of further improving diagnosis precision, the image resolution is preferably 1 million pixels or more, more preferably 2 million pixels or more, and further preferably 8 million pixels or more. The higher the resolution of the image is, the greater the burden becomes in processing for calculating the above-described evaluation value for all of the pixels. However, according to the configuration of the above embodiment, it is possible to suppress the processing burden in evaluation value calculation, and therefore the advantageous effect of the configuration of the present embodiment is remarkable in the situation of processing a high-definition image.

Although all of the pixels in the image are subjected to processing in the special image generation processing in the above embodiment, pixels with a very high luminance, pixels with a very low luminance, or the like may be excluded from the target of processing. Specifically, the precision of the evaluation value can be improved by performing evaluation value calculation on only pixels determined to have a luminance in a predetermined reference luminance range, for example.

As described in the above embodiment, various types of light sources can be used as the light source used in the electronic endoscope system 1. However, a mode is also possible in which the type of light source is limited depending on the observation target of the electronic endoscope system 1 or the like (e.g., a laser type is excluded as the type of light source).

Also, regarding the color components used for evaluation value calculation, a mode is possible in which the calculation of the evaluation value using hue and saturation is excluded.

In the above embodiment, in processing step S12 (setting of reference axis AX) in FIG. 2, the axis connecting the pixel correspondence point a and the origin (0,0) is set as the reference axis AX (mucous membrane variation axis), but the reference axis AX setting method is not limited to this.

Figure 7:
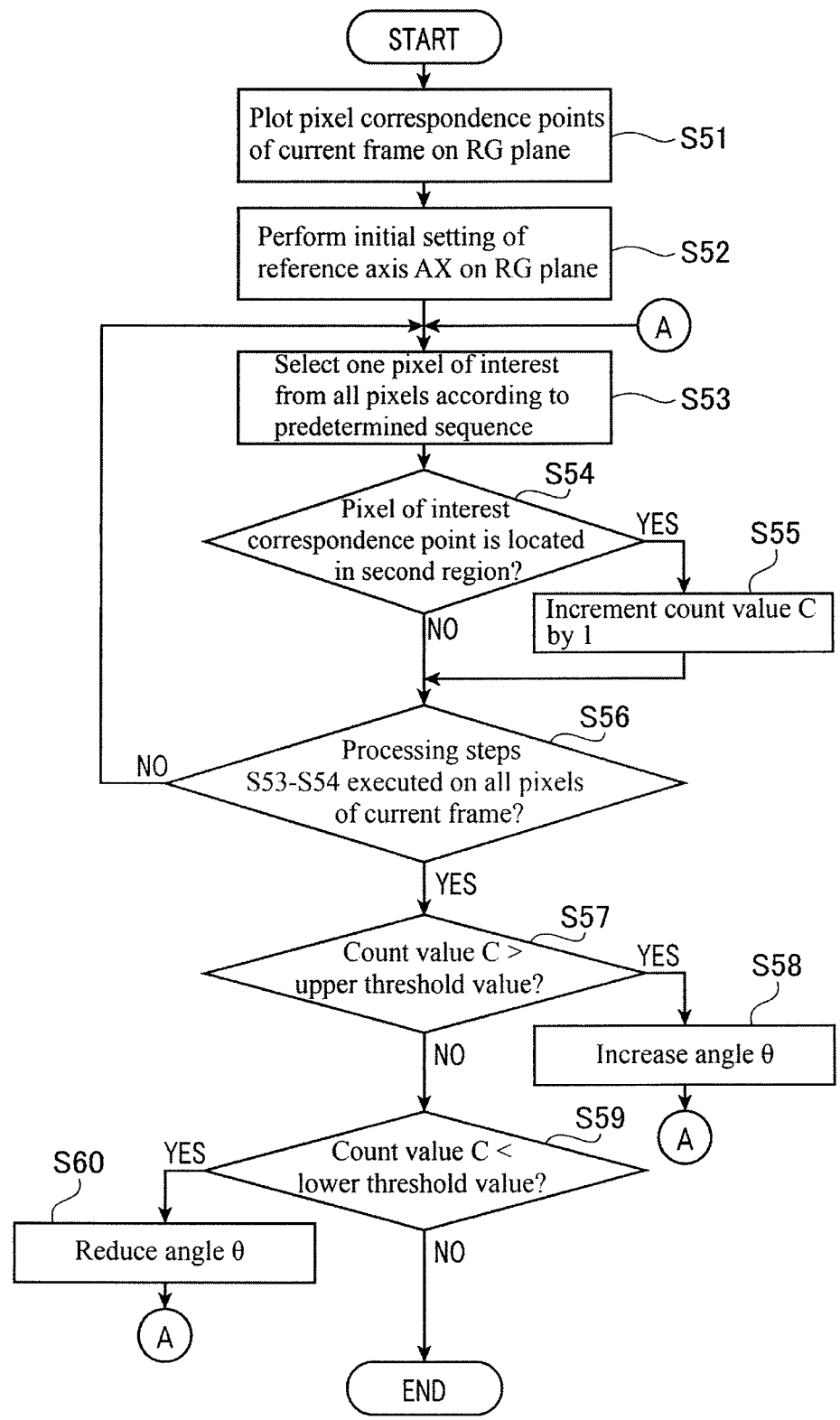
FIG. 7 is a diagram showing a flowchart of mucous membrane variation axis (reference axis AX) setting processing, which is executed in a variation of the embodiment of the present invention.
Figure 8:
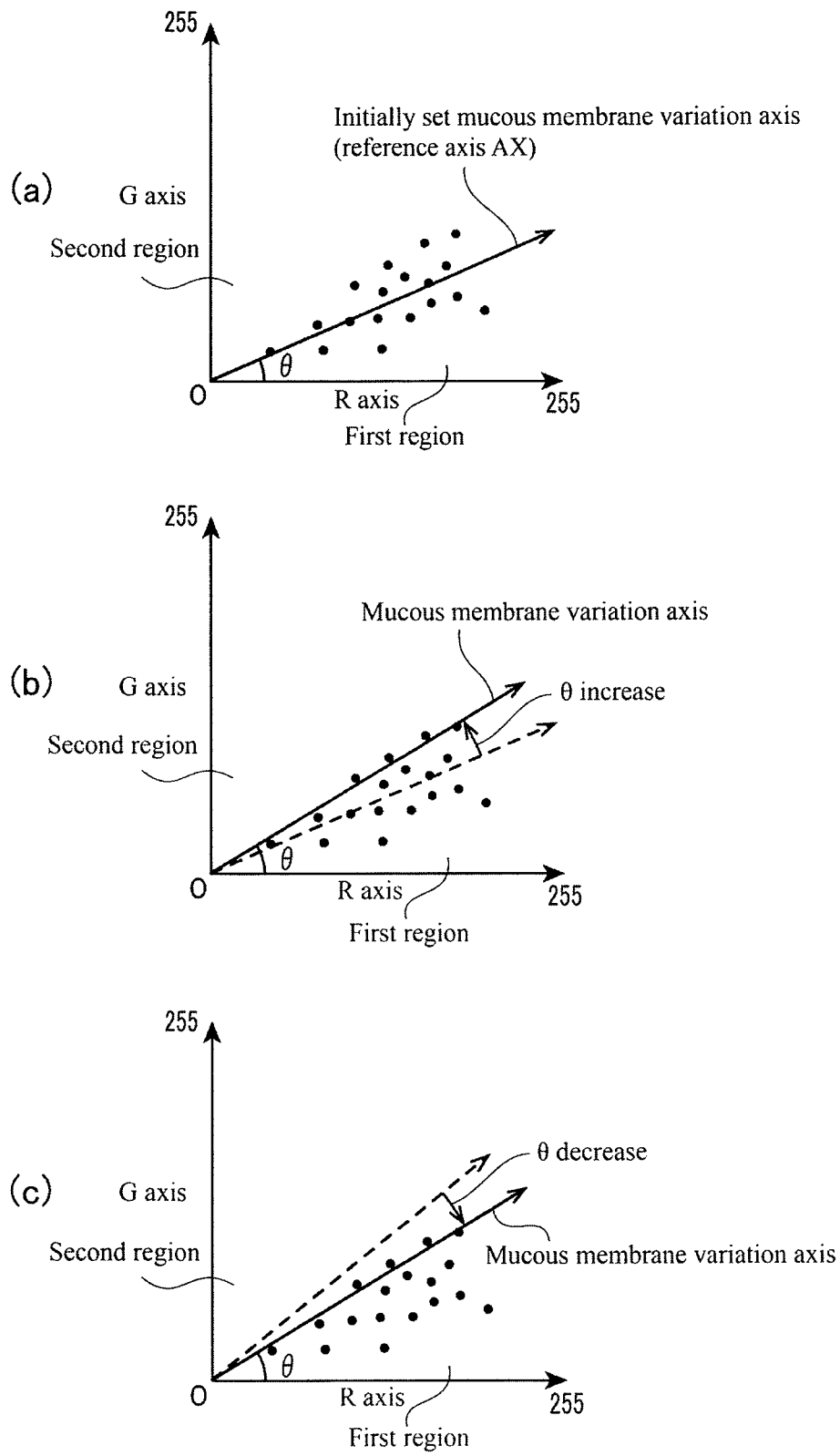
FIG. 8 is a diagram for assisting a description of setting processing according to the variation in FIG. 7.

FIG. 7 shows a flowchart of reference axis AX setting processing that is executed in a variation of the above embodiment. Also, FIG. 8(a) to FIG. 8(c) are diagrams for assisting the description of the setting processing according to the present variation. The special image generation processing according to the present variation is substantially the same as the special image generation processing according to the above embodiment, with the exception that the reference axis AX is set by executing the setting processing shown in FIG. 7.

S51 in FIG. 7 (Plotting of Pixel Correspondence Points)

In this processing step S51, pixel correspondence points of the current frame are plotted on the RG plane.

S52 in FIG. 7 (Initial Setting of Reference Axis AX)

In this processing step S52, as shown in FIG. 8(a), the reference axis AX is initially set on the RG plane. Initial setting data regarding the reference axis AX is stored in advance in a predetermined storage medium such as a memory 222. Note that in the following, the angle formed by the reference axis AX and the R axis is denoted by θ.

S53 in FIG. 7 (Selection of Pixel of Interest)

In this processing step S53, one pixel of interest (pixel of interest correspondence point) is selected from among all of the pixels in accordance with a predetermined sequence.

S54 in FIG. 7 (Position Determination)

In the present variation, in S14 (calculation of degree of inflammation) in FIG. 2, the pixel of interest correspondence points located in the region between the reference axis AX and the R axis (first region) are used in degree of inflammation calculation, and the pixel of interest correspondence points located in the region between the reference axis AX and the G axis (second region) are not used in degree of inflammation calculation. In this processing step S54, it is determined whether or not the pixel of interest correspondence point that was selected in processing step S53 (selection of pixel of interest) is located in the second region.

S55 in FIG. 7 (Count Processing)

This processing step S55 is executed if it is determined in processing step S54 (position determination) that the pixel of interest correspondence point is located in the second region (S54: YES). In this processing step S55, a count value C of a counter in the special image processing circuit 230 is incremented by one. Note that the count value C is reset to zero at the time when the execution of the setting processing shown in FIG. 7 is started, for example.

S56 in FIG. 7 (Determination of Completion of Execution of Processing for all Pixels)

In this processing step S56, it is determined whether or not processing steps S53 to S54 have been executed on all of the pixel correspondence points that were plotted in processing step S51 (plotting of pixel correspondence points).

If a pixel correspondence point not yet subjected to processing steps S53 to S54 remains (S56: NO), the setting processing shown in FIG. 7 returns to processing step S53 (selection of pixel of interest) in order to execute processing on the next pixel of interest correspondence point.

S57 in FIG. 7 (Determination Regarding Count Value C)

Step S57 of this processing is executed if it is determined in processing step S56 (determination of completion of execution of processing for all pixels) that processing steps S53 to S54 have been executed on all of the pixel correspondence points (S56: YES). In this processing step S57, it is determined whether or not the count value C is greater than a predetermined upper threshold value.

S58 in FIG. 7 (Increasing of Angle θ)

Step S58 of this processing is executed if it is determined in processing step S57 (determination regarding count value C) that the count value C is greater than the predetermined upper threshold value (S57: YES). In this case, there are too many pixel of interest correspondence points located in the second region (in other words, pixels of interest that are not to be used in degree of inflammation calculation), and it is difficult to calculate an inflammation evaluation value with high precision. In view of this, in this processing step S58, the angle θ is increased as shown in FIG. 8(b) so as to reduce the number of pixel of interest correspondence points located in the second region to an appropriate number.

Note that the amount of increase in the angle θ may be a fixed value, or may be appropriately set according to the magnitude of the count value C. In the latter case, the amount of increase in the angle θ is set larger the larger the count value C is, for example.

After the execution of this processing step S58, the count value C is reset to zero, and the setting processing shown in FIG. 7 returns to processing step S53 (selection of pixel of interest). Then, processing steps S53 to S56 are executed with respect to the reference axis AX after the increase in the angle θ (i.e., the number of pixel of interest correspondence points located in the second region after the increase in the angle θ is counted), and then processing step S57 (determination regarding count value C) is executed. The processing of processing steps S53 to S58 is repeated until the count value C decreases to the predetermined upper threshold value or lower.

S59 in FIG. 7 (Determination Regarding Count Value C)

Step S59 of this processing is executed if it is determined in processing step S57 (determination regarding count value C) that the count value C is lower than or equal to the predetermined upper threshold value (S57: NO). In this processing step S59, it is determined whether or not the count value C is smaller than a predetermined lower threshold value.

S60 in FIG. 7 (Decreasing of Angle θ)

Step S60 of this processing is executed if it is determined in processing step S59 (determination regarding count value C) that the count value C is smaller than the predetermined lower threshold value (S59: YES). In this case, there are too few pixel of interest correspondence points located in the second region (in other words, pixels of interest that are not to be used in degree of inflammation calculation), and there is a risk that the reference axis AX has not been set appropriately (e.g., the reference axis AX is located at a position largely deviating from the region in which pixel of interest correspondence points are densely distributed). In view of this, in this processing step S60, the angle θ is reduced as shown in FIG. 8(c) so as to increase the number of pixel of interest correspondence points located in the second region to an appropriate number.

Note that the amount of decrease in the angle θ may be a fixed value, or may be appropriately set according to the magnitude of the count value C. In the latter case, the amount of decrease in the angle θ is set larger the smaller the count value C is, for example.

After the execution of this processing step S60, the count value C is reset to zero, and the setting processing shown in FIG. 7 returns to processing step S53 (selection of pixel of interest). Then, processing steps S53 to S56 are executed with respect to the reference axis AX after the decrease in the angle θ (i.e., the number of pixel of interest correspondence points located in the second region after the decrease in the angle θ is counted), processing step S57 (determination regarding count value C) is executed, and then processing step S59 (determination regarding count value C) is executed. The processing of processing steps S53 to S60 is repeated until the count value C rises to the predetermined lower threshold value or higher.

By repeating the increase or decrease in the angle θ, the number of pixel of interest correspondence points located in the second region falls within an appropriate range (between the lower threshold value and the upper threshold value) (S60: NO). Accordingly, highly precise calibration (setting of the reference axis AX that can change due to differences between models, change over time, and the like in the electronic endoscope 100) is achieved.

In the special image generation processing shown in FIGS. 2 and 7, an inflammation evaluation value is calculated for a captured image, but in another embodiment, an inflammation evaluation value may be calculated for a moving image (i.e., over multiple frames).

Figure 9:
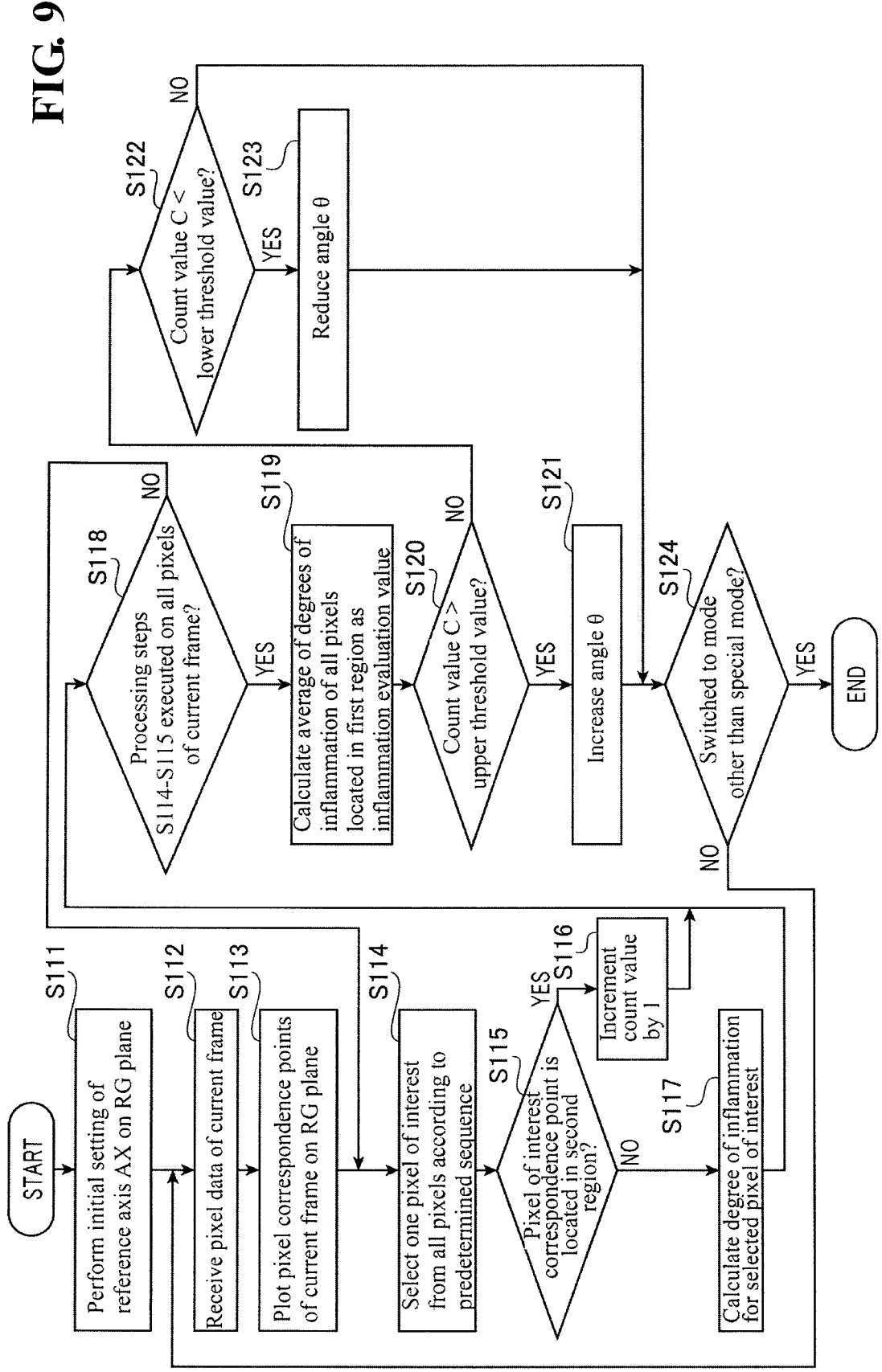
FIG. 9 is a diagram showing a flowchart of inflammation evaluation value calculation processing according to another embodiment of the present invention.

FIG. 9 shows a flowchart of inflammation evaluation value calculation processing according to another embodiment. The inflammation evaluation value calculation processing shown in FIG. 9 is started at the time when the operating mode of the electronic endoscope system 1 is switched to the special mode, for example. Note that in the case of this other embodiment, as is described below, only the inflammation evaluation value is included in the content displayed on the display screen of the monitor 300, but in this other embodiment as well, the inflammation evaluation value may be displayed on the display screen of the monitor 300 along with an endoscopic image such as an overlay image, similarly to the above embodiment.

S111 in FIG. 9 (Initial Setting of Reference Axis AX)

In this processing step S111, the reference axis AX is initially set on the RG plane with use of initial setting data that is stored in the memory 222 or the like.

S112 in FIG. 9 (Input of Pixel Data of Current Frame)

In this processing step S112, pixel data for each pixel of the current frame is received from the pre-stage signal processing circuit 220.

S113 in FIG. 9 (Plotting of Pixel Correspondence Points)

In this processing step S113, pixel correspondence points of the current frame are plotted on the RG plane.

S114 in FIG. 9 (Selection of Pixel of Interest)

In this processing step S114, one pixel of interest (pixel of interest correspondence point) is selected from among all of the pixels in accordance with a predetermined sequence.

S115 in FIG. 9 (Position Determination)

In this processing step S115, it is determined whether or not the pixel of interest correspondence point that was selected in processing step S114 (selection of pixel of interest) is located in the second region.

S116 in FIG. 9 (Count Processing)

Step S116 of this processing is executed if it is determined in processing step S115 (position determination) that the pixel of interest correspondence point is located in the second region (S115: YES). In this processing step S116, the count value C is incremented by one. Note that the count value C is reset to zero for each frame (e.g., each time processing step S112 (input of pixel data of current frame) is executed for the target frame), for example.

S117 in FIG. 9 (Calculation of Degree of Inflammation)

This processing step S117 is executed if it is determined in processing step S115 (position determination) that the pixel of interest correspondence point is not located in the second region (in other words, is located in the first region) (S115: NO). In this processing step S117, the degree of inflammation is calculated for the pixel of interest that was selected in processing step S114 (selection of pixel of interest).

S118 in FIG. 9 (Determination of Completion of Execution of Processing for all Pixels)

In this processing step S118, it is determined whether or not processing steps S114 to S115 have been executed for all of the pixels in the current frame.

If a pixel not yet subjected to processing steps S114 to S115 remains (S118: NO), the procedure in the inflammation evaluation value calculation processing in FIG. 9 returns to processing step S114 (selection of pixel of interest) in order to execute processing steps S114 to S115 on the next pixel of interest.

S119 in FIG. 9 (Calculation of Inflammation Evaluation Value)

This processing step S119 is executed if it is determined in processing step S118 (determination of completion of execution of processing for all pixels) that processing steps S114 to S115 have been executed on all of the pixels of the current frame (S118: YES). In this processing step S119, an average value obtained by averaging the degrees of inflammation of the pixels calculated in processing step S117 (degree of inflammation calculation) (in other words, only the pixels located in the first region) is calculated as the overall inflammation evaluation value for the captured image, and is displayed on the display screen of the monitor 300.

S120 in FIG. 9 (Determination Regarding Count Value C)

In this processing step S120, it is determined whether or not the count value C is greater than a predetermined upper threshold value.

S121 in FIG. 9 (Increasing of Angle θ)

This processing step S121 is executed if it is determined in processing step S120 (determination regarding count value C) that the count value C is greater than the predetermined upper threshold value (S120: YES). In this case, there are too many pixel of interest correspondence points located in the second region, and it is difficult to calculate an inflammation evaluation value with high precision. In view of this, in this processing step S120, the angle θ is increased so as to reduce the number of pixel of interest correspondence points located in the second region to an appropriate number.

S122 in FIG. 9 (Determination Regarding Count Value C)

This processing step S122 is executed if it is determined in processing step S120 (determination regarding count value C) that the count value C is lower than or equal to the predetermined upper threshold value (S120: NO). In this processing step S122, it is determined whether or not the count value C is smaller than a predetermined lower threshold value.

S123 in FIG. 9 (Decreasing of Angle θ)

This processing step S123 is executed if it is determined in processing step S122 (determination regarding count value C) that the count value C is smaller than the predetermined lower threshold value (S122: YES). In this case, there are too few pixel of interest correspondence points located in the second region, and there is a risk that the reference axis AX has not been set appropriately. In view of this, in this processing step S123, the angle θ is reduced so as to increase the number of pixel of interest correspondence points located in the second region to an appropriate number.

S124 in FIG. 9 (Determination of End of Inflammation Evaluation Value Calculation Processing)

In this processing step S124, it is determined whether or not the operator has switched from the special mode to another mode such as the normal mode, for example. If the operator has not switched to another mode (S124: NO), the inflammation evaluation value calculation processing in FIG. 9 returns to processing step S112 (input of pixel data of current frame) in order to perform the calculation and display of an inflammation evaluation value for the next frame. If the operator has switched to another mode (S124: YES), the inflammation evaluation value calculation processing in FIG. 9 ends.

According to this other embodiment, the reference axis AX is successively adjusted when performing moving image capturing in which the imaging conditions and imaging region successively change (In other words, the reference axis AX is re-set for each frame. Note that the reference axis AX is maintained when the number of pixel of interest correspondence points located in the second region falls within the appropriate range (between the lower threshold value and the upper threshold value).). For this reason, even in a situation in which the image conditions and imaging region successively change, the inflammation evaluation value is successively calculated with high precision.

What is claimed is:

1. An electronic endoscope system comprising:
a memory that stores instructions; and
a processor that, when executing the instructions stored in the memory, performs the operations of:
a plotting operation configured to plot pixel correspondence points, which correspond to pixels that constitute an intracavitary color image that has a plurality of color components, on a target plane according to color components of the pixel correspondence points, the target plane defined by a first color axis and a second color axis intersecting at an origin of a predetermined color space;
an axis setting operation configured to set a reference axis in the target plane based on pixel correspondence points plotted on the target plane, the reference axis extending from the origin of the predetermined color space to a said pixel correspondence point that is located on a line segment connecting the end point of the first color axis and the end point of the second color axis and that is located the closest to the end point of the second color axis; and
an evaluation value calculating operation configured to calculate a prescribed evaluation value with respect to the intracavitary color image based on a positional relationship between the reference axis and the pixel correspondence points.

2. The electronic endoscope system according to claim 1, wherein the first color axis is an R component axis.

3. The electronic endoscope system according to claim 2, wherein the second color axis is a G component axis.

4. The electronic endoscope system according to claim 1, wherein:
the plotting operation plots the pixel correspondence points in a predetermined section of the target plane, the section is defined by first and second axes that pass through the origin, letting the origin be a start point of the first and second axes, and other ends of the first and second axes be end points of the axes, and the axis setting operation detects a pixel correspondence point that is located on a line segment connecting the end point of the second axis and the end point of the first axis and that is closest to the end point of the second axis, and sets an axis that connects the detected pixel correspondence point and the start point as the reference axis.

5. The electronic endoscope system according to claim 1, wherein:

the axis setting operation partitions the target plane into a first region and a second region using the reference axis, the evaluation value calculating operation calculates the prescribed evaluation value using pixel correspondence points plotted in the first region, and the axis setting operation sets the reference axis in a manner according to which the number of pixel correspondence points plotted in the second region falls in a predetermined range.

6. The electronic endoscope system according to claim 1, wherein the axis setting operation sets the reference axis each time the color image is captured by an image capturing unit, or only at a predetermined timing.

7. The electronic endoscope system according to claim 1, wherein the axis setting operation calculates a provisional reference axis each time a predetermined timing is reached, and sets the reference axis based on the provisional reference axes calculated at the timings.

8. The electronic endoscope system according to claim 1, wherein the prescribed evaluation value is a numerical representation of a portion in a body cavity.

9. An evaluation value calculation device comprising:

a memory that stores instructions; and a processor that, when executing the instructions stored in the memory, performs the operations of:

a plotting operation configured to plot pixel correspondence points, which correspond to pixels that constitute an intracavitary color image that has a plurality of color components, on a target plane according to color components of the pixel correspondence points, the target plane defined by a first color axis and a second color axis intersecting at an origin of a predetermined color space;

an axis setting operation configured to set a reference axis in the target plane based on pixel correspondence points plotted on the target plane, the reference axis extending from the origin of the predetermined color space to a said pixel correspondence point that is located on a line segment connecting the end point of the first color axis and the end point of the second color axis and that is located the closest to the end point of the second color axis; and an evaluation value calculating operation configured to calculate a prescribed evaluation value with respect to the captured image based on a positional relationship between the reference axis and the pixel correspondence points.

* * * * *